United States Patent [19]
Olsen

[11] Patent Number: 5,322,523
[45] Date of Patent: Jun. 21, 1994

[54] OSTOMY COUPLING

[75] Inventor: Hans Olsen, Brønshøj, Denmark

[73] Assignee: Coloplast A/S, Denmark

[21] Appl. No.: 820,587

[22] PCT Filed: Jul. 20, 1990

[86] PCT No.: PCT/DK90/00192

§ 371 Date: Mar. 19, 1992

§ 102(e) Date: Mar. 19, 1992

[87] PCT Pub. No.: WO91/01118

PCT Pub. Date: Feb. 7, 1991

[30] Foreign Application Priority Data

Jul. 21, 1989 [DK] Denmark .............................. 3618/89

[51] Int. Cl.$^5$ .............................................. A61F 5/448
[52] U.S. Cl. ...................................... 604/338; 604/339
[58] Field of Search ................................ 604/332–342

[56] References Cited

U.S. PATENT DOCUMENTS

| | | | |
|---|---|---|---|
| 2,796,063 | 6/1957 | Smelser | 604/342 |
| 2,958,326 | 11/1960 | Nelsen | 604/341 |
| 4,518,389 | 5/1985 | Steer et al. | 604/339 |
| 4,623,338 | 11/1986 | Larson | 604/339 |
| 4,775,373 | 10/1988 | Steer | 604/339 X |
| 4,850,985 | 7/1989 | Edwards et al. | 604/339 |
| 4,892,530 | 1/1990 | Steer | 604/338 |
| 4,963,136 | 10/1990 | Steer et al. | 604/339 |
| 4,973,324 | 11/1990 | Steer | 604/342 |
| 5,026,360 | 6/1991 | Johnsen et al. | 604/339 X |
| 5,180,377 | 1/1993 | Holtermann | 604/342 |

FOREIGN PATENT DOCUMENTS

| | | |
|---|---|---|
| 255310 | 2/1988 | European Pat. Off. . |
| 841197 | 6/1952 | Fed. Rep. of Germany ...... 604/337 |
| 2201345 | 9/1988 | United Kingdom . |
| 2215212 | 9/1989 | United Kingdom . |

Primary Examiner—Randall L. Green
Assistant Examiner—Mary Beth O. Jones
Attorney, Agent, or Firm—Ostrolenk, Faber, Gerb & Soffen

[57] ABSTRACT

The present invention relates generally to an ostomy coupling having a first part for attachment to a patient and a second part secured to a collection bag and coupled in a tight-fitting relationship with the first part. A radially deformable locking ring mutually retains the first and second parts together. The locking ring is an open ring having opposed ends. The ends are positionable in a pre-locked first mutual position, in which the coupled first and second parts are mutually loosely connected and a second mutual position in which the coupled first and second parts are mutually locked The locking ring is movable with one of the first and second parts.

10 Claims, 7 Drawing Sheets

OSTOMY COUPLING

BACKGROUND OF THE INVENTION

The present invention relates to an ostomy coupling comprising a first part with a neck, a second part with a collar adapted to be coupled in tight-fitting relationship with the neck of the first part, one of the parts being intended to be attached to a patient, the other part being secured to a collection bag, and a locking ring for mutually retaining the parts.

The invention is primarily constructed as a lockable coupling for retaining ostomy equipment, such as bags for collection of evacuations for surgically formed, artificial intestinal orifices, and for retaining closure-like locking devices for such artificial bodily orifices, but it is also suited for retaining ostomy, incontinence, wound and fistula drainages, including retaining bags for collection of urea from incontinent natural or artificial urinary orifices.

Such couplings are usually annular and the part intended to be attached to a patient (in the following called the patient part) is often provided with a plate or flange applied with an adhesive by which the patient part is adhered to the patient's skin and which is generally changed at an interval of several days. The second part of the coupling, which is secured to a bag for collecting faeces, in the following called the bag part, must for obvious reasons be completely tight-fitting to the patient part.

GB 2 201 345 discloses a coupling for ostomy bags in which a locking or latch ring must be flexed axially in order to couple and release the coupling parts. Such axial flexing requires axial pulling forces perpendicular to the wearer's skin, which can be very painful to the wearer.

Manipulation of the coupling parts during assembly and disassembly may cause great pain, especially to newly operated ostomy patients, and consequently it is important that such manipulation transfers as few and small force loads as at all possible to the patient.

Consequently, it is desirable to provide a coupling of the kind described with a locking mechanism so that assembly and disassembly may be performed without causing heavy loads, while the coupling parts are retained together by the locking mechanism which can be brought into and out of engagement in an easy way without transferring any appreciable force to the patient. It is furthermore important that the coupling, besides the patient part and the bag part, comprises no other loose or separate parts, so that assembly and disassembly can be performed quickly, and in a simple and safe way.

SUMMARY OF THE INVENTION

It is the object of the present invention to provide such an ostomy coupling.

According to the invention the object is achieved by an ostomy coupling comprising a first part attached to a patient and a second part secured to a collection bag, with a radial, deformable locking ring mutually retaining the parts in a tight-fitting relationship.

By the locking ring being an open ring movably retained with respect to one of the parts so that it is deformable between a first position and a second position, in which the locking ring assumes two different diameters and the coupled parts are mutually loosely connected and mutually locked, respectively, it is achieved that the locking ring and the part to which it is retained, is perceived by the user as being one single part. The locking ring can then be so positioned that in the position in which the coupled parts are mutually loosely connected it can by one single movement be made to assume the other position in which the parts are mutually locked and vice versa. By means of such an ostomy coupling comprising three parts the correct positioning of the locking ring is ensured, and the patient only needs to place the bag part correctly relative to the patient part without worrying about whether the locking ring is also correctly positioned, whereafter the parts are locked with the locking ring.

By the locking ring being elastically deformable it is achieved that when released the ring is capable by itself of assuming the position in which the coupled parts are mutually, loosely connected. The patient consequently only needs to perform one single release operation before the coupled parts can be disassembled.

By an ostomy coupling having a first and second locking mechanism, the locking ring can be released from that part to which it is secured, and similarly during manufacture it can in a simple way be positioned on and retained with respect to the same part. By the two locking mechanisms being independent of each other the patient in particular obtains the advantage that the second locking mechanism is not unintentionally activated when operating the first locking mechanism. Thus it is ensured that the locking ring is constantly retained with respect to the coupling part in question.

It is advantageous to retain the locking ring to the patient part, the latter as mentioned being changed less frequently than the bag part.

Through the complementary engagement faces of the bag part and the locking ring the bag part in its locked state can be retained in a minutely preselected position, and that in case of force load, e.g. the force of gravity from a full bag, it will not undergo deformation or tilt, but remain centered, and thus at all times ensuring a tight-fitting coupling.

When the first and second parts of the coupling have complementary engagement faces adapted for axial engagement, no frictional force has to be surmounted during assembly and disassembly, which is the case with faces having substantially radial engagement.

This ensures the lowest possible force load and pain for the patient. These axial engagement faces can advantageously be slightly conical, achieving a centering effect during assembly.

A particularly efficient seal at the engagement faces is achieved when at least one of these faces is provided with one or more circular ribs such a rib by elastic deformation can easily be capable of adapting itself to small unevennesses, if any, in the opposite engagement face, thus ensuring an efficient seal.

In order to avoid spilling of faeces when changing the bag, the engagement face of the patient part may along its periphery by provided with an axially outwardly projecting edge, which will act as a barrier.

Furthermore, the locking ring has radially resilient tongues. When changing the bag these tongues will ensure the centering of the locking ring in relation to the patient part, whereby the positioning of the bag part is facilitated.

The locking ring can be retained to one of the coupling parts by means of flexible straps. Hereby the locking ring and the coupling part in question can be integrally moulded, and by suitable choice of material and dimensions, the straps will be able to contribute to the elastic resiliency of the locking ring.

In the following the invention is described in more detail, with reference being made to the drawings.

DETAILED DESCRIPTION OF THE INVENTION

Figure 1:
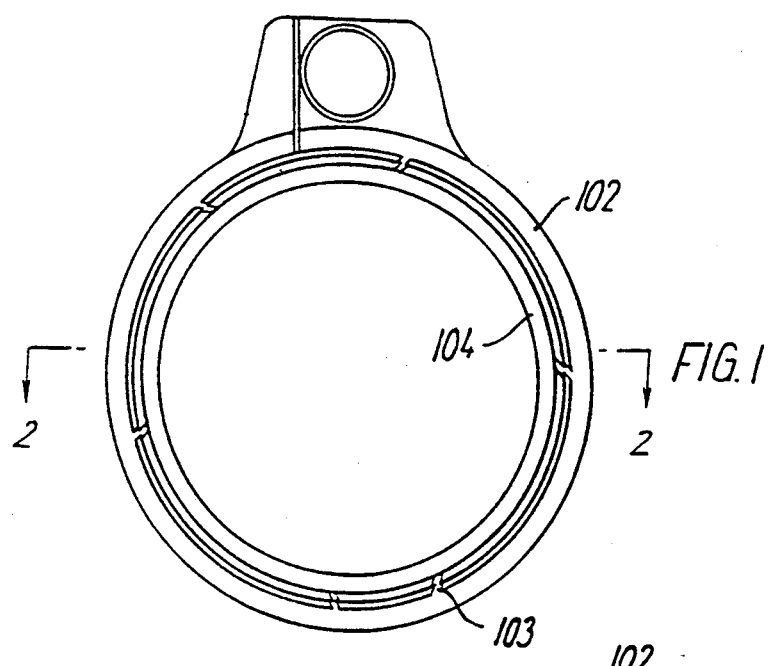
FIG. 1 shows a top view of a first embodiment of the invention.
Figure 2:
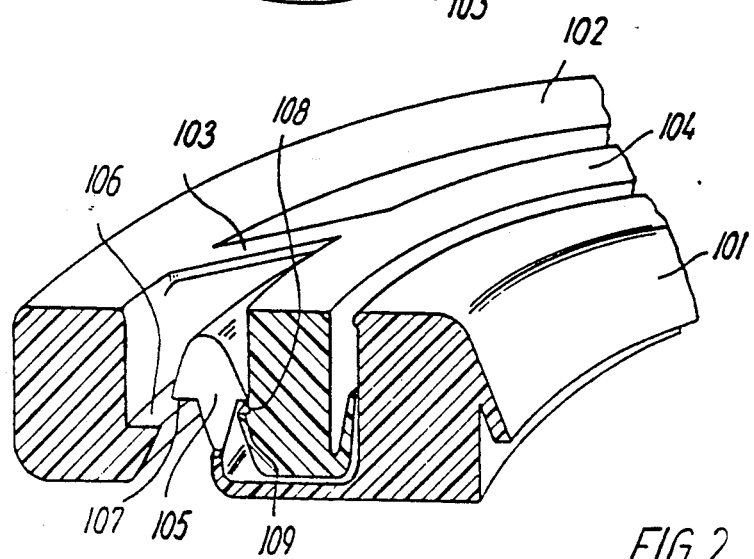
FIG. 2 is a cross-section of a part of the coupling along lines of FIG. 1.
Figure 3:
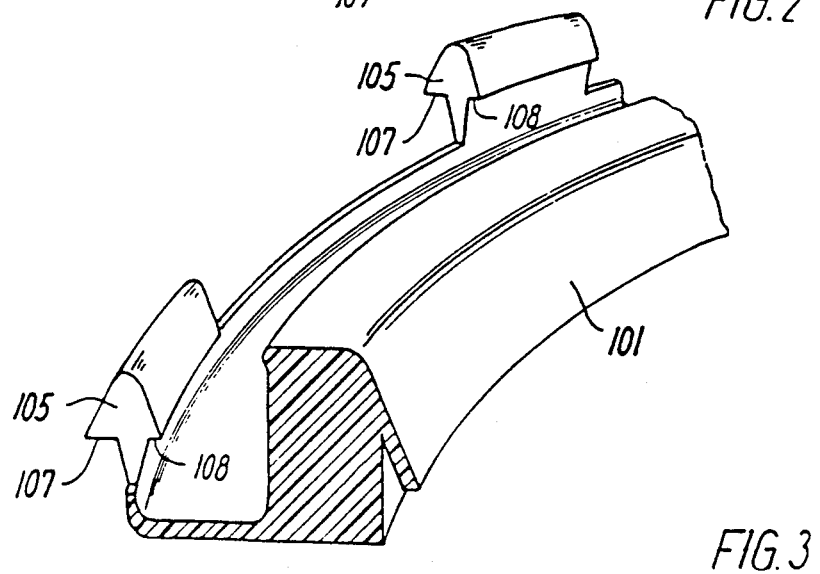
FIG. 3 is a cross-section of the part of the coupling which is intended to be attached to a patient, and which is shown in FIG. 2.

FIGS. 1-3 show a first embodiment of the invention having an annular patient part 101 with a short neck which is secured to a plate or flange (not shown) which is adapted for being attached to the patient's skin around an ostomy orifice by means of an adhesive. A locking ring 102 is connected by means of flexible straps 103 to a ring 104 being secured to a bag (not shown) for collecting faeces. The locking ring 102 and the annular bag part 104 are positioned at either side of the engagement taps 105 constituting parts of the patient part 101. The locking ring 102 and the bag part 104 are shown in FIG. 2 in a pre-locked position, allowing the bag part 104 with the locking ring 102 and the patient part 101 to be assembled and disassembled. The locking ring 102 is flexible and can be tightened from the position shown in FIG. 2 so that a radially inwardly directed protrusion 106 on the inner side of the locking ring 102 engages with a complementary, radially outwardly directed protrusion 107 on the engagement taps 105. The engagement taps 105 are flexible and also include radially inwardly directed protrusions 108 which engage with complementary and radially outwardly directed protrusions 109 on the bag part 104. Thus, the bag is fixed relative to the patient part 101, especially ensuring that they cannot be separated.

Figure 4:
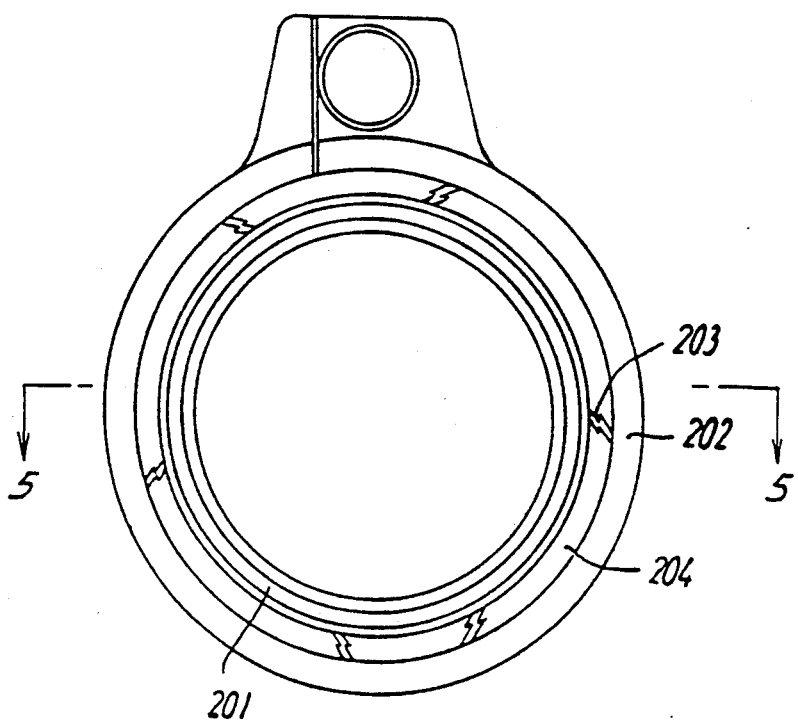
FIG. 4 shows a top view of another embodiment of the invention.
Figure 5:
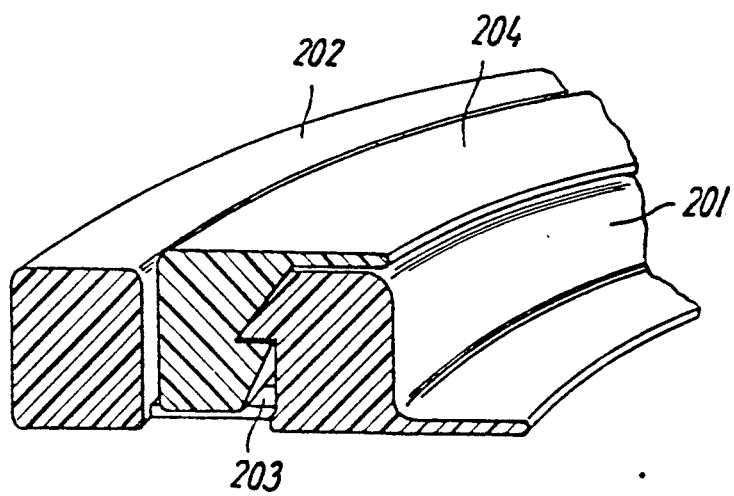
FIG. 5 illustrates a cross-sectional view of a part of the embodiment along lines 5—5 in FIG. 4.

FIGS. 4 and 5 show a variant of the above embodiment. A locking ring 202 is secured by means of flexible straps 203 to an annular patient part 201. In FIG. 5, the locking ring 202 is shown in a locked state, in which an annular bag part 204 is retained in a position inseparable from patient part 201.

Figure 6:
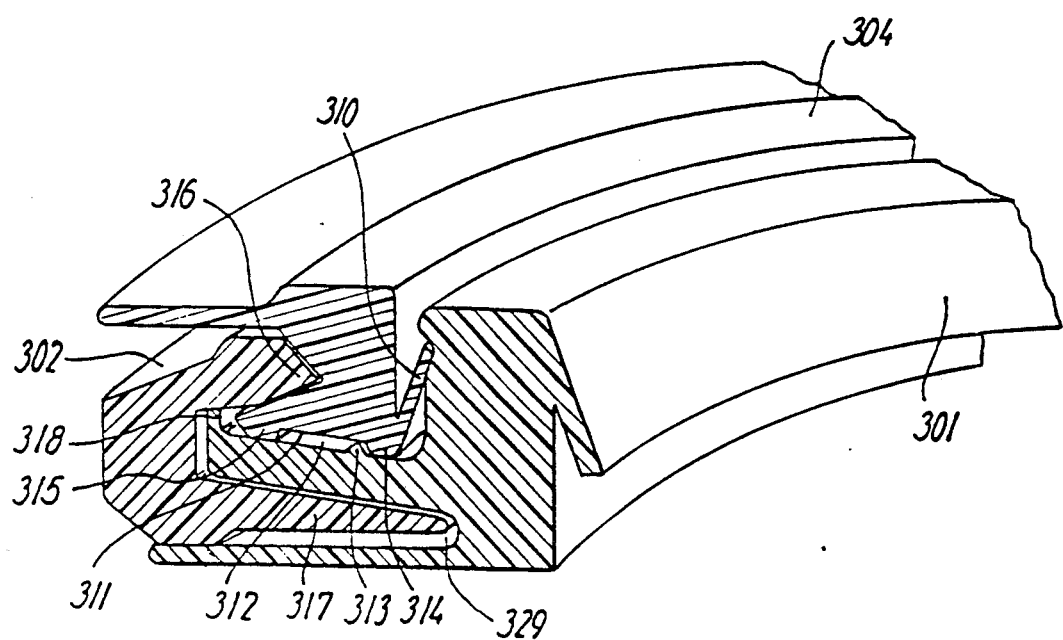
FIG. 6 is a cross-sectional view of a preferred embodiment of the invention.

The preferred embodiment of the invention shown in FIG. 6 has an annular patient part 301 with a short neck having its under side adapted for being secured onto the adhesive plate or flange, by which the patient part 301 is positioned on the patient's skin around an ostomy orifice. An annular bag part 304 is adapted at its upper side for being secured to a bag (not shown) for the collection of faeces from the ostomy orifice. An elastic resilient locking ring 302 is shown in a locked position in which it retains the bag part 304 in an inseparable position relative to the patient part 301.

The seal between the bag part 304 and the patient part 301 of the coupling is constituted partly by a radially flexible lip ring 310 which abuts against a corresponding face on the patient part 301, partly by axial engagement between an engagement face 311 on the bag part 304 and an engagement face 312 on the patient part 301. The engagement face 312 of the patient part is shown with an annular rib 313, and similarly also the engagement face of the bag part is shown with two such ribs 314 and 315. As a result of force load from the locking ring 302 in the axial direction, these ribs ensure a more reliable seal, as the axial contact faces are thus relatively small so that the axial coupling force will somewhat deform the ribs, and consequently small unevennesses, if any, on the contact faces are smoothened out as a consequence of the resulting elastic deformation of the materials.

It is further seen that the engagement faces 311 and 312 are substantially conical with a relatively large opening angle. The conical shape of the engagement faces contribute to the centering of the bag part 304 in relation to the patient part 301 when assembling these parts, so that the risk of eccentric assembly of the parts is significantly reduced.

The locking ring has an inwardly projecting part 316 shaped as an outwardly open V, and which then tightening and locking the locking ring engages with a corresponding recess in the bag part. When pressing the locking ring this V-shape produces the necessary axial coupling force between the bag part 304 and the patient part 301. Further, this shape also provides support for the bag part so that a possible force load from e.g. a full ostomy bag cannot deform the locking ring, whereby complete seal and maximum user conform are ensured at all times.

From FIG. 6 it is also seen that along the periphery of the engagement face 312 of the patient part 301 there is an axially outwardly projecting edge 318 which during bag changing prevents or at least significantly reduces spilling of faeces.

Figure 7:
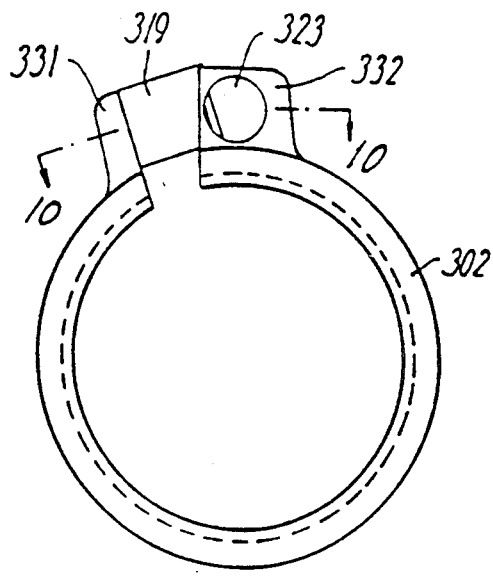
FIG. 7 shows the locking ring in the embodiment shown in FIG. 6 in a pre-locked position.
Figure 8:
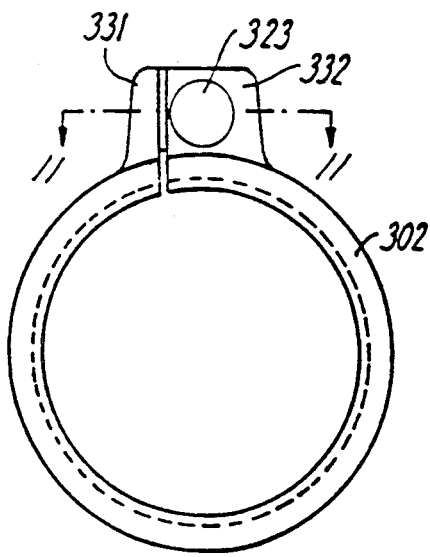
FIG. 8 shows the locking ring in FIG. 7, in a locked position.
Figure 9:
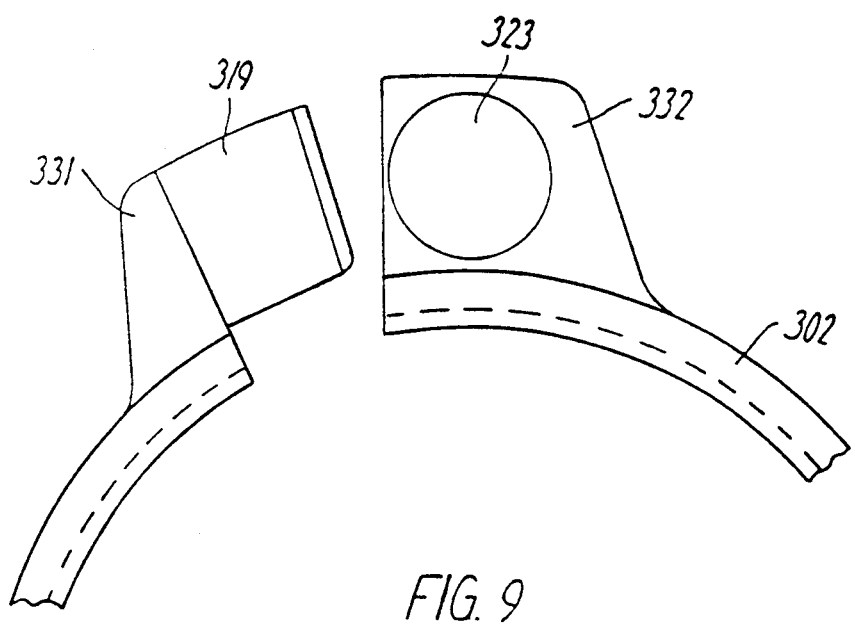
FIG. 9 shows a part of the locking ring of FIGS. 6-8 in a completely unlocked position.

The locking effect, i.e. the tightening of the bag part 304 and the patient part 301 is derived from the locking ring 302. In FIGS. 7-9 it is seen that the locking ring 302 is broken by an almost radial cut so as to be capable of assuming the three positions shown in FIGS. 7-9, respectively. FIG. 7 shows the locking ring in a pre-locked position, which is the position when the coupling is supplied to the user and when it is attached to the user's body, and which permits changing of the ostomy bag, as the coupled parts here are mutually loosely connected. FIG. 8 shows the locking ring 302 in a locked position in which it is also shown in FIG. 6, and in which the bag part 304 is retained in position in relation to the patient part 301. FIG. 9 shows the locking ring 302 in a completely open position, which position the locking ring has during manufacture by moulding, and in which it can be positioned on the patient part 301. The locking ring 302 is preferably moulded of an elastic resilient material and will thus naturally seek to assume the completely open position shown in FIG. 9. When locking mechanisms for the locked and pre-locked position, respectively, of the ring are released, the locking ring will consequently by itself spring open and assume the pre-locked or the completely unlocked position, respectively.

In each of the three positions of the locking ring, the pre-locked, the locked and the completely unlocked position, respectively, the locking ring has three different diameters.

As is seen in FIG. 6, the locking ring 302 has an inwardly projecting part or edge 317 which has a smaller internal diameter than that of the part 316 of the locking ring. These internal diameters are so adapted that in the pre-locked position of the ring in FIG. 7, the diameter of the part 316 of the locking ring which retains the bag part is increased precisely so much compared to the locked position that the bag part 304 and the patient part 301 can easily be assembled and disassembled by a mutual axial movement. In this pre-locked position of the locking ring, the part 317 of the locking ring is still in engagement with the corresponding recess or groove 325 in the patient part 301, and the locking ring is thus retained on the patient part.

Not until the locking ring 302 is opened to assume its completely unlocked position in FIG. 9 can the locking ring be released from the patient part 301.

Figure 10:
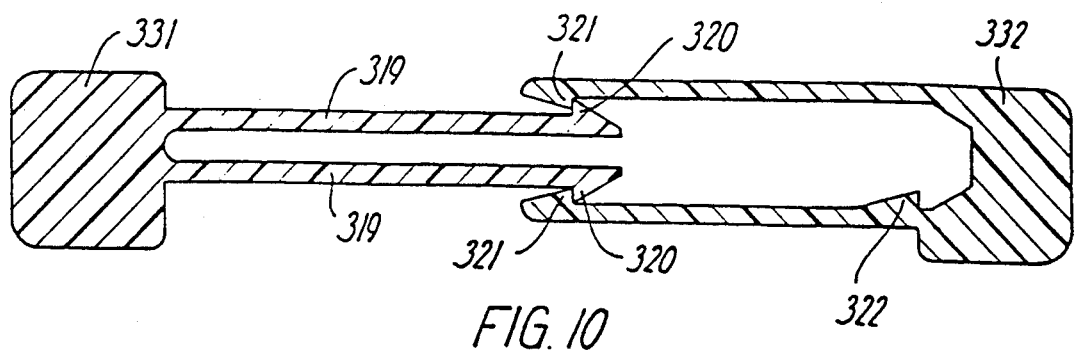
FIG. 10 is a cross-section of the locking mechanism of the locking ring in the pre-locked position along lines 10—10 in FIG. 7.
Figure 11:
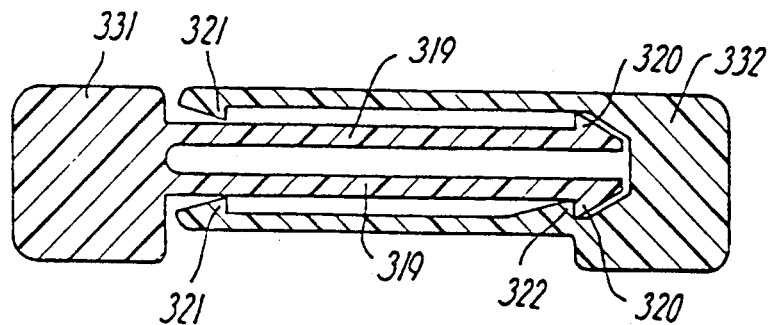
FIG. 11 is a cross-section of the locking mechanism of the locking ring in the locked position along lines 11—11 in FIG. 8, FIGS. 12 and 13 show parts of an alternative embodiment of the locking ring in a pre-locked and locked position, respectively.

FIG. 10 shows a section through the pre-locked locking mechanism of the locking ring along the line X—X in FIG. 7. FIG. 11 shows a section through the locked locking mechanism of the locking ring along the line XI—XI in FIG. 8. On a radially outwardly projecting protrusion 331, the locking ring is provided with two elastic, axially resilient flaps 319 which at their tips have axially outwardly projecting hooks 320, which in the pre-locked position in FIG. 10 abut against corresponding inwardly directed hooks 321, and in the locked position in FIG. 11 abut against a hook 322. The hooks 321 and 322 are provided on a radially outwardly projecting protrusion 332. In order to activate this locking mechanism so as to pass from the pre-locked position in FIG. 10 to the locked position in FIG. 11, the two protrusions 331 and 332 of the locking ring are pressed together, and one of the hooks 320 enters into a clicking-engagement with the hook 322. Through an opening 323, shown in FIGS. 7-9, it is possible by a slight touch of a finger to disengage the hooks 320 and 322, whereby the locking mechanism due to its resiliency reassumes the pre-locked position shown in FIG. 10.

In order to release the locking mechanism completely, the hooks 320 must be released from the hooks 321, and with a suitable construction of the hooks this is done when the protrusion 331 with the flaps 319, by a radial movement, are lifted free of the hooks 321 so that the locking ring assumes the unlocked position shown in FIG. 9.

Figure 14:
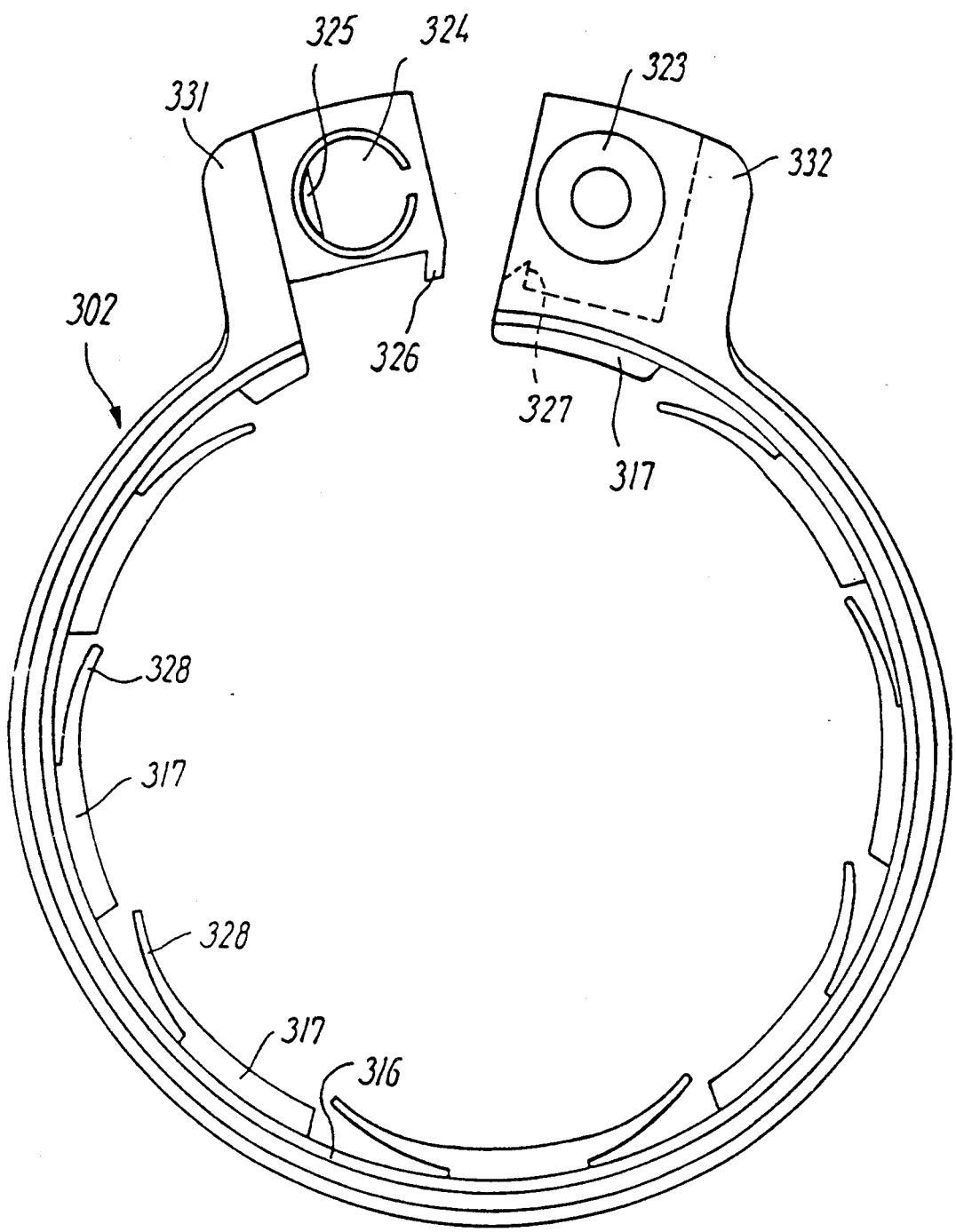
FIG. 14 is a top view of a preferred embodiment of the locking ring according to the invention in a completely unlocked position.

FIG. 14 shows the preferred embodiment of the locking ring according to the invention in its completely unlocked state. A flap 324 here corresponds to the flaps 319 in FIGS. 10 and 11, and the flap 324 has an axially outwardly projecting hook 325 corresponding to the hooks 320 in FIGS. 10 and 11. Further, the locking ring in FIG. 14 has on each separate one of the protrusions 331 and 332, two hooks 326 and 327. In the pre-locked position of the locking ring these hooks are in mutual engagement, and the locking ring may be made to assume its completely unlocked position in that the hook 326 by a radial movement is released from the hook 327. From the completely unlocked position the locking ring is easily made to assume both the pre-locked and locked position by pressing the locking ring.

In FIG. 14 it is further seen that some of the parts 317 of the locking ring are provided with radially inwardly projecting resilient tongues 328, the tips of which lie on the circle having a diameter which is smaller than that of the parts 317. These resilient tongues 328 will also in the pre-locked position of the locking ring be in radial contact with the bottom of the annular groove 329 in the patient part 301, and thus also in the pre-locked position of the locking ring center the locking ring.

Figure 12:
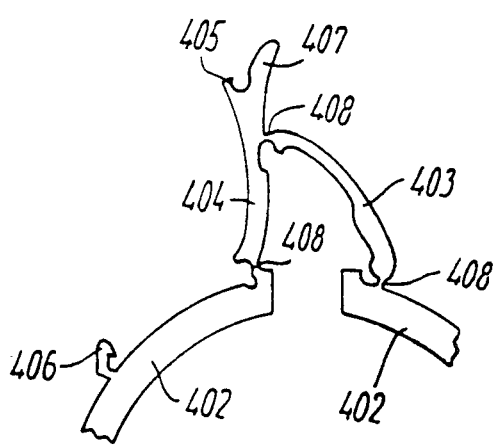
Figure 13:
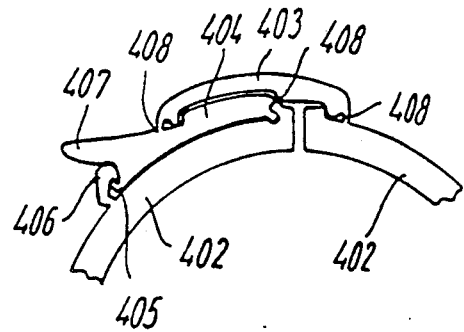

FIGS. 12 and 13 show a fourth embodiment of the locking mechanism of the locking ring. A locking ring 402 is open along a radial cut, and on both sides of the cut two rocker arms 403 and 404 are hingedly secured. By hinges 408, provided as thin material bridges, the rocker arms 403 and 404 are mutually connected as well as connected to the locking ring 402 on respective sides of the radial cut. The locking ring 402 is shown in an open position in FIG. 12, allowing the ostomy bag to be changed in FIG. 13 in a locked position, in which an ostomy bag can be retained in position in relation to a patient part (not shown). The rocker arm 404 has a hook 405 which passes into engagement with a hook 406 on the locking ring 402.

The locking mechanism is released from the locked position shown in FIG. 13 by touching a tap 407 with a finger so that the hooks 405 and 406 pass out of engagement. The hooks 405 and 406 may be so formed that the tap 407 must be activated either radially or axially in order to release the hooks 405 and 406 from their mutual engagement.

Figure 15:
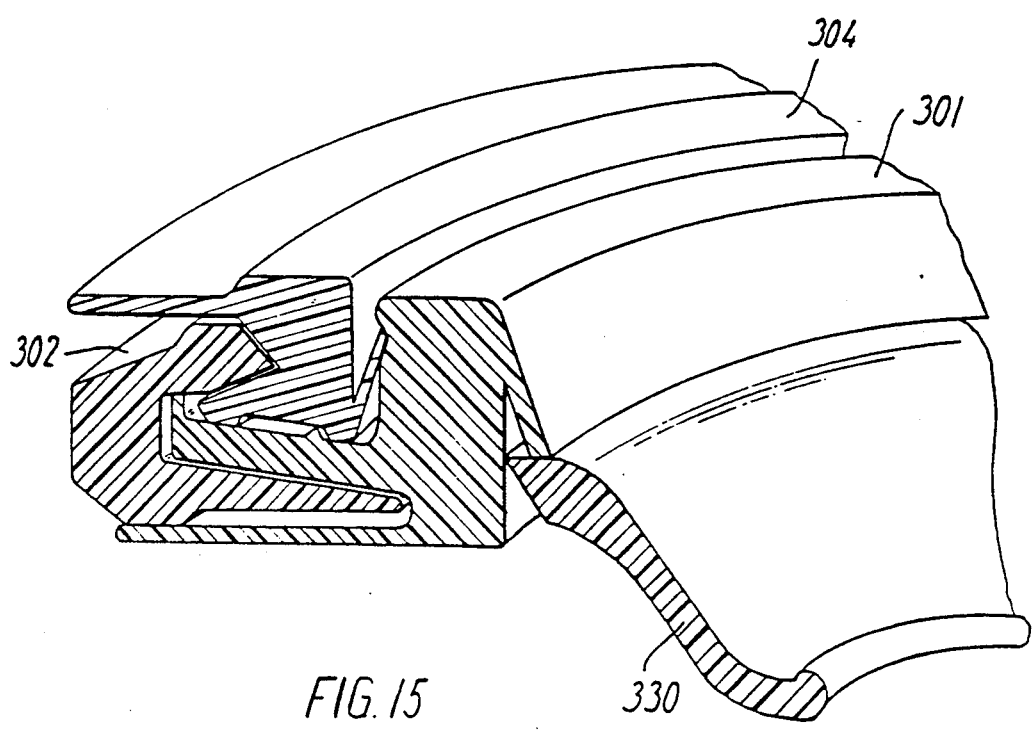
FIG. 15 is a cross-sectional view of the coupling in FIG. 6, provided with a convex ring.

Finally, FIG. 15 shows how the coupling according to the invention can be combined with a so-called convex ring 330. A convex ring is often used in connection with the ostomies which do not project from the body, but lie in the same plane or even below surface level, and it serves to keep the adhesive plate fixed to the skin so as to prevent faeces material from seeping out from below.

The coupling according to the invention may be made of ordinary plastic materials used for coupling in connection with ostomy and bandaging purposes, e.g. polyethylene or EVA-materials. To ensure that the locking ring is flexible and elastically deformable, but not stretchable, it may e.g. be made of a plastic material having a somewhat higher E-modulus, e.g. polypropylene or ABS, or be provided with a fibre reinforcement of such materials.

I claim:
1. An ostomy coupling comprising:
   a first part for attachment to a patient;
   a second part secured to a collection bag and coupled in a tight-fitting relationship with the first part;
   a radially deformable locking ring for mutually retaining said first and second parts together in the tight-fitting relationship, the locking ring being an open ring having opposed ends, the ends being positionable in a pre-locked first mutual position in which the locking ring has a first diameter and the coupled first and second parts are mutually loosely connected, and a second mutual position in which the locking ring has a second diameter and the coupled first and second parts are mutually locked; and means for retaining the locking ring movably with one of the first and second parts.

2. An ostomy coupling according to claim 1, wherein the locking ring is elastically deformable.

3. An ostomy coupling according to claim 1, further including a first locking mechanism for locking the ends of the locking ring in the first and second mutual positions, and a second locking mechanism which is independent of the first locking mechanism for positioning the ends of the locking ring in a third mutual position in which the locking ring has a third diameter and the locking ring is released from one of the first and second parts.

4. An ostomy coupling according to claim 1, wherein the locking ring is retained with the first part.

5. An ostomy coupling according to claim 4, wherein the second part has a radially, outwardly opened V-shaped groove, and the locking ring has a radially inwardly protruding portion having a shape complementary to the V-shaped groove for engaging the V-shaped groove.

6. An ostomy coupling according to claim 1, wherein the first part has a first conical engagement face and the second part has a second conical engagement face which is complementary to and engages the first conical engagement face, when the first and second parts are retained together.

7. An ostomy coupling according to claim 6, wherein at least one of the first and second engagement faces is provided with one or more ridges for contacting the respective complementary engagement face.

8. An ostomy coupling according to claim 6, wherein the first engagement face of the first part has an axially protruding rib along its outer periphery.

9. An ostomy coupling according to claim 4, wherein the means for retaining the locking ring comprises radially resilient tongues for cooperation with a groove disposed in the first part.

10. An ostomy coupling according to claim 1, wherein the means for retaining the locking ring comprises integral flexible straps connectable with the first part.

* * * * *